(12) United States Patent
Small et al.

(10) Patent No.: US 6,623,455 B2
(45) Date of Patent: Sep. 23, 2003

(54) MEDICAL FLUID DELIVERY SYSTEM

(75) Inventors: James R. Small, Beavercreek, OH (US); Frank M. Fago, Mason, OH (US); Gary S. Wagner, Taylor Mill, KY (US); Mitchell A. Smith, Cincinnati, OH (US); Joseph B. Tyson, Silverton, OH (US)

(73) Assignee: Mallinckrodt, Inc., St. Louis, MO (US)

( * ) Notice: Subject to any disclaimer, the term of this patent is extended or adjusted under 35 U.S.C. 154(b) by 37 days.

(21) Appl. No.: 09/788,791

(22) Filed: Feb. 20, 2001

(65) Prior Publication Data

US 2001/0009994 A1 Jul. 26, 2001

Related U.S. Application Data

(62) Division of application No. 09/353,563, filed on Jul. 14, 1999.

(51) Int. Cl.[7] .............................................. A61M 37/00
(52) U.S. Cl. ...................... 604/131; 604/132; 604/506; 141/18
(58) Field of Search .......................... 128/DIG. 12, 912, 128/898, DIG. 1; 604/411–415, 403, 85, 86, 239–241, 500, 507, 506, 131, 132, 141, 143, 151–153, 65, 67, 118, 217; 141/2, 18, 311 R, 329, 285, 301, 302, 382–389, 392

(56) References Cited

U.S. PATENT DOCUMENTS

| 441,238 A | 11/1890 | Guptill | |
|---|---|---|---|
| 553,234 A | 1/1896 | Finot | |
| 1,223,243 A | 4/1917 | Bessesen | |
| 1,831,668 A | 11/1931 | Juhl | |
| 3,051,173 A | 4/1962 | Johnson et al. | |
| 3,620,650 A | 11/1971 | Shaw | |
| 4,133,314 A | * 1/1979 | Bloom et al. | 128/272.3 |
| 4,187,890 A | * 2/1980 | Stach et al. | 141/27 |
| 4,253,501 A | * 3/1981 | Ogle | 141/27 |
| 4,398,909 A | * 8/1983 | Portnoff | 604/295 |
| 4,883,473 A | * 11/1989 | Thomas | 604/217 |
| 5,078,691 A | 1/1992 | Hamacher | |
| 5,122,121 A | 6/1992 | Sos et al. | |
| 5,188,610 A | 2/1993 | Rains | |
| 5,211,638 A | 5/1993 | Dudar et al. | |
| 5,328,463 A | 7/1994 | Barton et al. | |
| 5,334,141 A | * 8/1994 | Carr et al. | 604/50 |
| 5,334,170 A | 8/1994 | Moroski | 604/80 |
| 5,348,539 A | * 9/1994 | Herskowitz | 604/141 |
| 5,383,859 A | 1/1995 | Sewell, Jr. | |
| 5,395,340 A | * 3/1995 | Lee | 604/151 |
| 5,411,499 A | 5/1995 | Dudar et al. | 604/411 |
| 5,450,847 A | 9/1995 | Kämpfe et al. | |
| 5,533,978 A | 7/1996 | Teirstein | |

(List continued on next page.)

FOREIGN PATENT DOCUMENTS

| EP | 0 650 739 | 5/1995 | |
|---|---|---|---|
| EP | 0 852 152 | 7/1998 | |
| FR | WO 97/02853 | * 1/1997 | A61M/5/162 |
| WO | WO 99/15074 | 4/1999 | |

Primary Examiner—Brian L. Casler
Assistant Examiner—Jennifer Maynard
(74) Attorney, Agent, or Firm—Wood, Herron & Evans, L.L.P.

(57) ABSTRACT

A system to provide a specified volume of a medical fluid from a bulk source to a dose and/or delivery container for injection into a patient. The fluid path between the bulk container and the delivery container is physically separated at a connecting site before fluid is injected from the delivery container into the patient. The bulk container may be a bag or bottle, and the delivery container may be a syringe or bag. A bag delivery container may be contained in a pressurizeable chamber and fluid may be delivered by providing pressure to a membrane in the chamber contacting a wall of the bag. The system may be automated.

19 Claims, 3 Drawing Sheets

U.S. PATENT DOCUMENTS

| | | |
|---|---|---|
| 5,569,181 A | 10/1996 | Heilman et al. |
| 5,569,208 A | 10/1996 | Woelpper et al. |
| 5,573,515 A | 11/1996 | Wilson et al. |
| 5,583,902 A | 12/1996 | Bae |
| 5,609,575 A * | 3/1997 | Larson et al. .................. 604/65 |
| 5,665,074 A | 9/1997 | Kelly |
| 5,728,086 A | 3/1998 | Niedospial, Jr. |
| 5,728,087 A | 3/1998 | Niedospial, Jr. |
| 5,738,671 A | 4/1998 | Niedospial, Jr. et al. |
| 5,772,635 A * | 6/1998 | Dastur et al. ................ 604/131 |
| 5,772,651 A | 6/1998 | De Haen et al. |
| 5,779,666 A | 7/1998 | Teirstein |
| 5,779,693 A | 7/1998 | Ropiak et al. |
| 5,806,519 A | 9/1998 | Evans, III et al. |
| 5,817,082 A | 10/1998 | Niedospial, Jr. et al. |
| 5,840,026 A | 11/1998 | Uber, III et al. |
| 5,843,037 A | 12/1998 | Uber, III |
| 5,868,710 A | 2/1999 | Battiato et al. |
| 5,885,216 A | 3/1999 | Evans, III et al. |
| 5,911,252 A * | 6/1999 | Cassel ........................ 141/234 |
| 5,968,014 A * | 10/1999 | Neftel et al. ................. 604/151 |
| 6,120,490 A * | 9/2000 | Neftel ........................ 604/411 |

* cited by examiner

MEDICAL FLUID DELIVERY SYSTEM

CROSS REFERENCE TO RELATED APPLICATIONS

This application is a division of commonly assigned, copending application Ser. No. 09/353,563, filed Jul. 14, 1999 and entitled MEDICAL FLUID DELIVERY SYSTEM, naming Small et al. as inventors, which is hereby incorporated by reference herein in its entirety; and is related to commonly assigned, copending application Ser. No. 09/353,217, filed Jul. 14, 1999 and entitled MEDICAL FLUID DELIVERY SYSTEM, naming Small et al. as inventors, which is hereby incorporated by reference herein in its entirety; and commonly assigned, copending application Ser. No. 09/353,521, filed Jul. 14, 1999, now U.S. Pat. No. 6,355,024, and entitled MEDICAL FLUID DELIVERY SYSTEM, naming Small et al. as inventors, which is hereby incorporated by reference herein in its entirety.

FIELD OF THE INVENTION

The invention relates generally to a device and method for providing a specified volume of a medical fluid from a bulk source to a dose container.

BACKGROUND OF THE INVENTION

Medical fluids are often packaged in standard size containers which are intended for single-use administration only. Typical containers include bags, bottles, vials, ampules, blister packs, etc. Once the factory seal on a medical fluid container is compromised, the Food and Drug Administration (FDA) mandates that the contents must be either administered within a set time interval or discarded. The underlying rationale for this regulation is that a medical fluid in an opened container has potentially been contaminated by either environmental pathogens or, if the container holds a multipatient fluid supply, by fluids from other patients. In multipatient or bulk fluid containers, the FDA has determined that if a continuous fluid path exists from the fluid to the patient, there is a possibility that the bulk fluid may be contaminated by exposure to a patient's fluids. Even a separating unit that is inserted in the fluid path from a fluid source to a patient, for example, a drip chamber such as a conventional intravenous drip chamber, a mixing chamber, a filter, one or more check valves, a peristaltic pump, and/or other flow control devices, is considered insufficient as a barrier for purposes of sterility. A problem with these devices is that a continuous thin fluid film may exist across the valve seat and/or check mechanism, which provides a contamination pathway for blood and pathogens from the patient. Therefore, only a system having a physical separation between the fluid supply source and the patient will meet FDA standards. While the strictness of this requirement has increased costs to the hospital and patient because it limits the fluid in a bulk container to a single use, it has also desirably decreased the incidence of nosocomial infections in patients.

In current medical practice for fluid administration to a patient, medical personnel typically either use prefilled containers that hold a single patient (unipatient) supply of medical fluid, or they transfer a unipatient fluid supply to a container from a bulk source of the fluid. Use of prefilled containers adds to the cost of the fluid and/or the procedure in which the fluid is used, such as a contrast agent used to enhance an imaging procedure. Transfer of a unipatient supply of fluid to a container from a bulk source, while less expensive, adds an additional point of potential contamination. Typically, a clinician or technologist draws fluid into a unipatient container using a transfer tube or needle or, in some cases, pours the fluid into the container. Such transfers are best performed using aseptic techniques in an attempt to reduce exposure of the fluid to nonsterile air or other sources of contamination, although this is not always done in practice. These techniques reduce the likelihood of contamination, but sufficient risks still exist such that using any fluid remaining in the bulk supply source is not generally considered an acceptable medical practice. If anything less than the entire volume of fluid from the bulk supply source is transferred, the remaining fluid should be discarded, resulting in wasted material.

Many types of fluids are administered to patients, including diagnostic, therapeutic and physiologic fluids. These fluids are administered under a variety of circumstances and for a variety of reasons. For example, imaging procedures such as ultrasound, magnetic resonance imaging (MRI), angiography and computed tomography frequently require image enhancement by contrast agents. Contrast agents are fluids that are normally administered intravascularly to provide a better view of the organ or system to be imaged. The dose of contrast agent is determined to achieve optimal imaging without providing excess agent, since the agent may be expensive and/or difficult to be efficiently removed from the body. The maximum dose is based upon pharmacokinetic limits, specified as milligrams (mg) of active ingredient per kilogram (kg) of patient body weight, and the minimum dose is predicated on achieving clinically viable diagnostic information from the imaging procedure. The range between the minimum dose and maximum dose varies widely for any given imaging procedure and patient. The optimal dose is influenced by a number of parameters, such as the image equipment technology, diagnostic techniques, clinician experience, and patient-specific parameters such as age, presence of pathology, physical proportions and other physiological parameters. For a "typical" 70 kg male patient in good health, a volume of about 100 ml of contrast agent is normally administered.

Use of fluid from a bulk source would facilitate timely administration of such fluids. For example, in imaging procedures it is common for physicians to administer excess x-ray contrast agent. Since higher blood concentrations of contrast agent generally yield improved images, physicians often reason that the excess volume is justified because it decreases the probability that a repeated image will be needed. Accordingly, there are now standardized protocols in which the maximum volume of x-ray contrast agent is used. The maximum volume is often based upon the available standard packaging sizes and concentrations from the manufacturers of contrast agents, and the entire content of the package is typically utilized regardless of its clinical necessity. This practice results in over medication and commensurate safety concerns for the patient, since adequate diagnostic information may be obtained at a dose that is well below even the maximum physiological threshold for a particular patient. Administration of excess agent may have nominal to severe pharmacological consequences, depending upon the condition of the patient and the identity of the agent.

Administration of less than the optimal volume of contrast agent may also have consequences, determined by the particular circumstances. For example, an optimal volume of agent may be required to be administered within a predetermined period of time. If the time of administration exceeds the predetermined time, the result may suboptimal imaging. Administration of a suboptimal volume may require performing the entire procedure at a later time and/or administering a second dose of agent. Suboptimal dosing thus exposes the patient to the possibility of receiving two doses of the agent in a short period of time, potentially compromising patient health and well being, and is a time- and cost-inefficient process.

A system is thus needed to provide a desired volume of a medical fluid from a bulk source in a medically acceptable, cost- and time-efficient manner.

SUMMARY OF THE INVENTION

The invention is directed to a medical fluid delivery system. The system comprises a bulk container for containing a bulk or multipatient fluid supply, a connecting site for access to the fluid in the bulk container, and a dose container for receiving a unipatient supply of fluid from the bulk container at the connecting site. The system may have a device to maintain sterility of the connecting site. The dose container may also function as a delivery container with either inflexible walls, e.g., a syringe, or at least one flexible wall, e.g., a bag. The system may contain a detector for the presence of air and may be automated.

The invention is also directed to a method of delivering a medical fluid. A bulk container for containing a multipatient fluid supply, a connecting site for access to the fluid supply in the bulk container, and a delivery container for receiving a unipatient supply of fluid from the bulk container at the connecting site and for delivering the fluid supply to a patient, is provided. A fluid flow is established from the bulk container to the delivery container at the connecting site to fill the delivery container. The delivery container is irreversibly disconnected from the bulk container at the connecting site and the fluid supply is thereafter delivered to the patient. The delivery container may have at least one flexible wall that contacts a pressurizeable chamber, with the unipatient fluid supply delivered to the patient from the delivery container by providing pressure to the flexible wall of the delivery container. The unipatient fluid supply may be a dose that has been customized for the patient by, for example, using an algorithm for patient and/or procedure specific data.

The invention is further directed to a method of maintaining sterility of a medical fluid that is dispensed from a bulk container to a dose and/or delivery container at a connecting site by providing a sterile environment at the connecting site. The connecting site may be enclosed in a controlled-access device with a filtered air flow adjacent the connecting site, or may be irradiated or provided with a chemical sterilant.

The invention is also directed to a sterile connector to access fluid in a bulk container. The connector has a first compartment to enclose a site to access fluid flow from a bulk container and a device to engage the access site to provide fluid flow to a connecting site in a second compartment. The connector also has the aforementioned second compartment for the connecting site and with a receiving projection and a conduit for providing a sterilant to the connecting site. The connector has a fluid evacuating channel which transverses the interior of the engaging and receiving projections, through which fluid from the bulk container is supplied to the receiving projection, and a channel for atmospheric pressure access which transverses the interior of the engaging projection and through which a filtered access to normal atmosphere is supplied to the bulk container. The second compartment terminates in a device to control access to the receiving projection. The controlled access device may be a door extending from the end of second enclosure, opening inwardly to expose the receiving projection and closing when not engaged.

The invention is still further directed to a medical fluid delivery system comprising a bulk container for containing a multipatient fluid supply and having a connector for providing a unipatient fluid supply to fill a flexible wall delivery container. The flexible wall container is connected to the system at the connecting site, either directly or indirectly, for filling with the unipatient fluid supply. After filling, the flexible wall container is irreversibly disconnected from the system at the connecting site and may then connect to a patient connector.

The invention is also directed to a medical fluid delivery system comprising a bulk container containing a multipatient fluid supply, having a connector for providing a unipatient fluid supply to a syringe at a connecting site and thereafter irreversibly disconnecting at the connecting site. The syringe may connect to a patient connector after disconnecting at the connecting site. The syringe may comprise a barrel for containing a unipatient fluid supply, a filling port that is operatively attached to the barrel and having a tube and a check valve, a discharge port, and a piston for discharging the fluid through the discharge port.

The invention is additionally directed to a method for providing a customized supply of a medical fluid to a patient. The customized supply is determined, then a bulk container containing a multipatient supply of the fluid and having a connecting site to access the fluid is provided and a delivery container for receiving the customized supply from the bulk container at the connecting site and for delivering the customized supply to the patient is also provided. A fluid flow from the bulk container to the delivery container is established by connecting the delivery container to the bulk container at the connecting site to provide the customized supply to the delivery container. The delivery container is irreversibly disconnected from the bulk container at the connecting site and thereafter the customized supply is delivered to the patient. In one embodiment, the system is automated.

The invention is also directed to a medical fluid delivery system providing at least one bulk container having at least a first port for attaching a first connector from the bulk container to a connecting site, and a unipatient supply container having at least a second port for receiving a unipatient supply of fluid at the connecting site and thereafter disconnecting at the connecting site. The system may further include a plurality of connectors, such as a second connector between the connecting site and the delivery container, a third connector to deliver the unipatient supply from the delivery container to a patient, etc.

The invention also includes a medical fluid delivery system in which the delivery container has at least one flexible wall and the fluid is delivered to a patient by providing a pressure to a pressurizeable chamber adjacent the flexible wall of the delivery container. The pressure may be hydraulic, mechanical, and/or pneumatic. The delivery container may be prefilled with the fluid, or may be filled using the system of the invention with fluid from a bulk container containing a multipatient supply of the fluid and having a connector to the delivery container.

The invention substantially reduces cross contamination from a bulk source to a patient, and from one patient to another patient receiving fluid from the same bulk source. The dose and/or delivery container is completely and irreversibly disconnected from a bulk container before connecting to a patient. Thus, there is no continuous fluid path from the bulk container to a patient. In one embodiment, the invention automatically fills and injects a predetermined volume of fluid that has been customized for a particular patient, resulting in cost and time efficiency and enhanced patient safety. The invention facilitates the safe administration of a medical fluid from a bulk container while minimizing waste of the fluid and pharmacological hazards due to insufficient or excess administration. Any type of fluid or combinations of fluids may be administered in the method of the invention, such as diagnostic fluids, therapeutic fluids, physiologic fluids, etc.

The objectives and other advantages of this invention will be further understood with reference to the following detailed description and examples.

DETAILED DESCRIPTION

Figure 1:
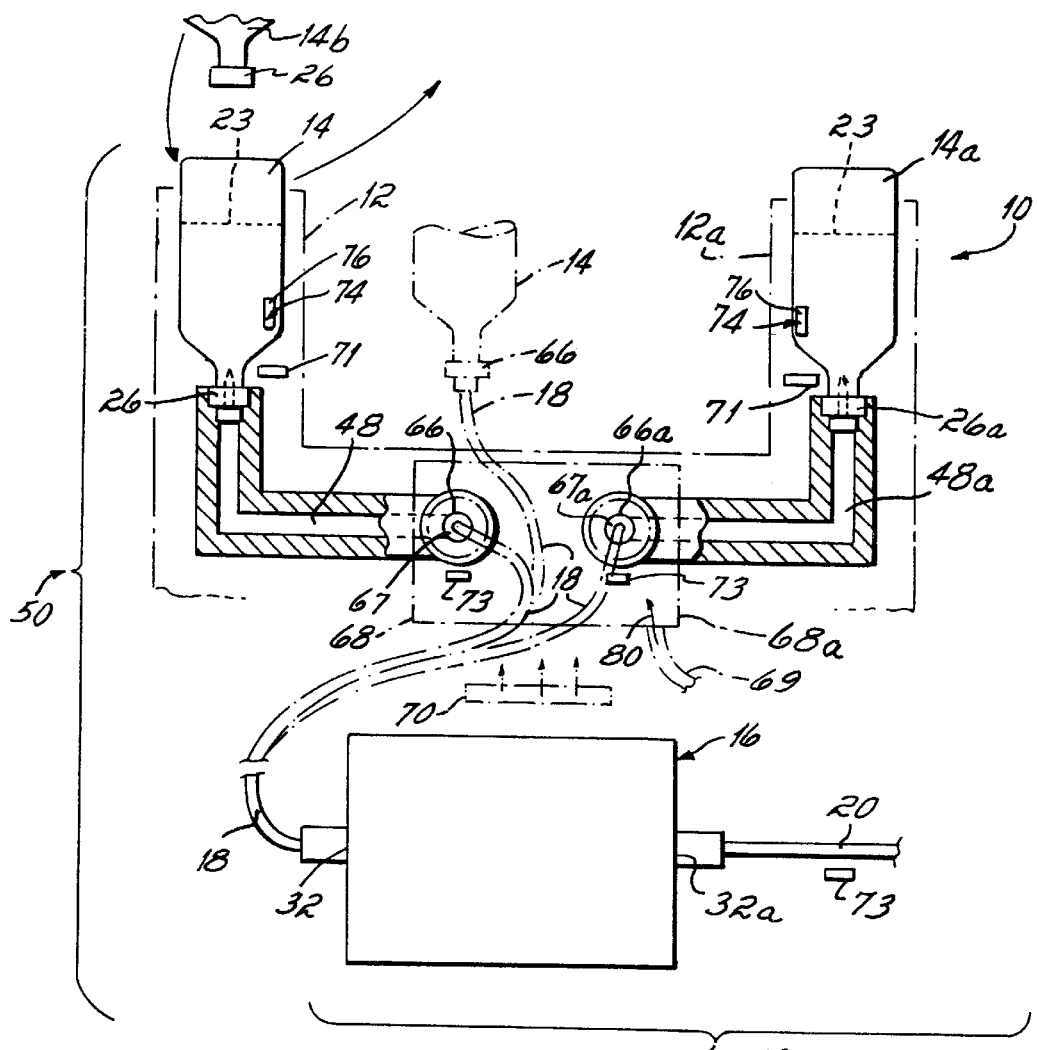
FIG. 1 is a schematic front-view of the medical fluid delivery system of the present invention.

A bulk container is defined herein as any container that contains and has means to access a bulk or multipatient supply of a fluid that can be administered to an individual. That is, a bulk container contains a volume of fluid that is greater than a volume to be administered at one time or to one individual, hereinafter referred to as a unipatient supply. The bulk container may contain variable volumes and may contain up to several liters of fluid. It may be manufactured of any biocompatible material, for example, glass or plastic and may be of any configuration, for example, having flexible or semi-flexible walls as in a plastic bag, or having inflexible walls as in a glass bottle.

A dose container is defined herein as any container that contains a unipatient or single supply of a medical fluid to be administered. The dose container may also be a delivery container for the fluid if the dose container is capable of both containing a unipatient supply of a medical fluid to be administered to an individual and also delivering the fluid to the individual without transfer of the fluid to a different container. That is, a dose container substantially contains or is filled with a unipatient supply of a medical fluid. A dose container may be an ampule, bag, vial, capsule, etc. that holds a unipatient fluid supply. A delivery container may be a syringe or bag that is capable of connecting, either directly or indirectly, to a patient to deliver the fluid. The dose and/or delivery container may be made of any biocompatible material such as glass or plastic and may hold any unipatient volume. While the dose and/or delivery container may be of any shape or configuration and may contain compartments, the flexible wall delivery container in particular may contain channels, grooves, or other structures to retard, enhance, direct or otherwise affect fluid flow. Such a container is disclosed in U.S. Pat. No. 5,779,693 entitled Flexible Plastic Container for the Containment and Delivery of Diagnostic Contrast Media and Parenteral Drug Formulations, which is expressly incorporated by reference herein in its entirety. A delivery container may have flexible or semi-flexible walls such as a bag, or inflexible walls such as a syringe.

A medical fluid is defined herein as any fluid or mixture of fluids that is administered to an individual for a therapeutic, diagnostic, physiologic and/or other medical purpose. The fluid is preferably sterile. Examples of such fluids include, but are not limited to, replenishing fluids such as normal saline, glucose, plasma, and/or electrolytes, diagnostic fluids such as contrast agents to enhance imaging by ultrasound (US), x-ray, computed tomography (CT), magnetic resonance imaging (MRI), and/or angiography, and therapeutic agents such as antibiotics and/or chemotherapeutic drugs. Fluids that are administered as mixtures of one or more diagnostic, therapeutic, physiologic and/or other agents may be mixed either prior to or during administration to an individual and may be contained in separate bulk containers in the system.

With reference to FIG. 1, the system 10 of the invention can be used to deliver any type of fluid 23 from a bulk source 14 to a dose and/or delivery container 16. The system 10 may also include delivering a fluid 23 from a dose and/or delivery container 16 directly or through a connector 20 to a patient (not shown). The system 10 of the invention thus comprises the transfer of fluid 23 from a bulk source 14 to a dose and/or delivery container 16 as one component path 50, the transfer of fluid 23 from a dose and/or delivery container 16 to a patient (not shown) as another component path 100, and the total path 50, 100 of transfer of fluid 23 from a bulk source 14 to a patient. The system 10 includes administration of a unipatient supply of fluid 23 that has been transferred from a bulk container 14 to a patient, i.e., using both component paths 50, 100, as well as administration of fluid 23 from a prefilled delivery container 16, such as a prefilled syringe or bag, i.e., using the component path 100, to a patient. The method of the total system 10 and/or its component paths 50, 100 may be automated.

In one embodiment of the invention, a plurality of bulk containers 14, 14a and connecting sites 66, 66a are contemplated. The bulk containers 14, 14a may contain the same or different fluids 23. It may be desirable for the bulk containers 14, 14a to contain the same fluid 23 so that depletion of a first bulk container 14 would allow fluid 23 to be drawn from the second bulk container 14a, thus not interrupting the process of fluid transfer. Alternatively, it may be desirable for the bulk containers 14, 14a to contain different fluids 23 to allow the same patient to receive more than one fluid 23 from a bulk source 14, 14a. An example of the later embodiment is a first bulk container 14 containing a contrast fluid and a second bulk container 14a containing saline to allow a patency check of a patient's vessel with saline. Saline may be drawn from bulk container 14a prior to administration of the contrast fluid from bulk container 14, and upon completion of an imaging procedure to flush the patient's vessel.

The fluid 23 in the bulk container 14 is accessible to the system 10 through a connecting site 66. The connecting site 66 may be integral with the bulk container 14, as shown in phantom. Alternatively, the connecting site 66 may be separated from and connected to the bulk container 14 by a connector 48. The bulk container 14, 14a may be sealed with a closure system 26, typically either an elastomeric stopper secured with a crimped metal seal that acts as a septum or a luer-type connection port that maintains sterility of the contained fluid 23 but allows access to the fluid 23. The bulk container 14, 14a may be placed in a holder 12, 12a for support, to facilitate its use, and/or to assist in removal of the maximal volume of fluid 23 such as where the bulk container 14, 14a is inverted in the holder 12, 12a.

The bulk container 14, 14a is positioned to allow the contained fluid 23 to be accessible at a connecting site 66, 66a which may be a septum 67, 67a. The system 10 may be configured with the connecting site 66, 66a integral with the bulk container 14, 14a, or separated from the bulk container 14, 14a and operably connected using tubing or other types of connectors 48, 48a. In the latter embodiment, a new sterile connector 48, 48a is attached at the connecting site 66, 66a upon installation of the new bulk container 14, 14a. The connector 48, 48a facilitates a single puncture of the closure system 26 on the bulk container 14, 14a to establish a sterile path of fluid 23. The connector 48, 48a may also provide a secondary linkage point that permits multiple connections and disconnections to or from the bulk container 14, 14a.

In the embodiment of the system 10 using a connector 48 from the bulk container 14 to the connecting site 66, the connector 48 remains attached to the bulk container 14 until the fluid 23 in the bulk container 14 is substantially depleted. At that time, or upon attainment of a preset level of fluid 23 in the first bulk container 14, the operatively attached connector line 18 to the dose and/or delivery container 16 disconnects at connecting site 66 and reconnects at connecting site 66a, operably connecting bulk container 14a by connector 48a, to access the fluid 23 contained in the second bulk container 14a. The fluid-depleted first bulk container 14 is removed from the system 10 and is replaced with a third new container 14b without interrupting the access of fluid 23 from bulk container 14a at connecting site 66a.

Figure 2:
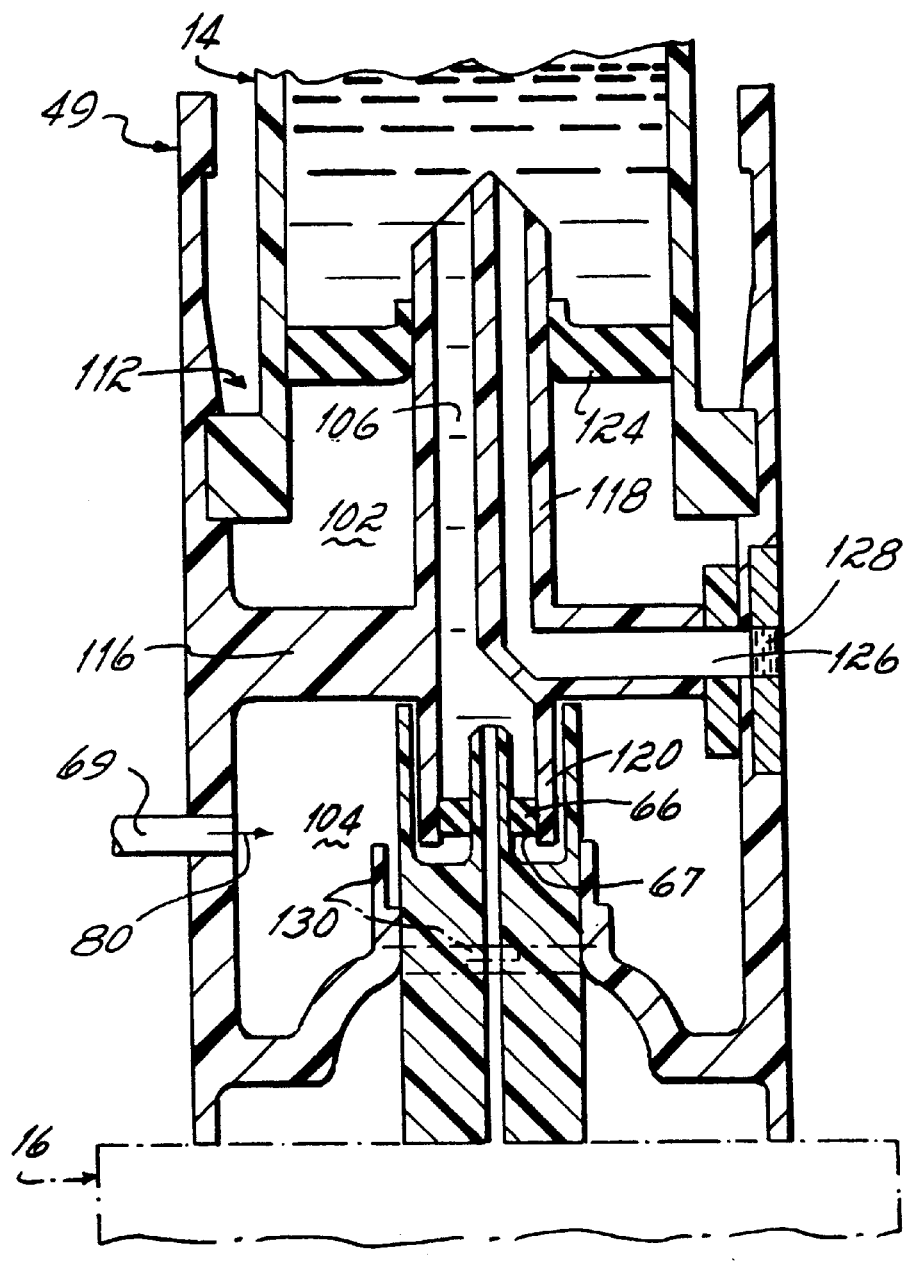
FIG. 2 is a schematic view of the sterility maintaining connection device.

Again with reference to FIG. 1, in one embodiment of the system 10 the connecting site 66, 66a is maintained sterile using one or more of several methods. With reference to FIG. 2, a sterility-maintaining shielding device 49 that both shields and provides a sterilant to the connecting site 66 may be used. In one embodiment, the device 49 encloses the connecting site 66 with a first compartment 102 and second compartment 104, the first compartment 102 enclosing a fluid channel 106 providing flow of fluid 23 from the bulk container 14 to the connecting site 66, and a second compartment 104 providing a flow of fluid 23 from the connecting site 66 to a dose and/or delivery container 16. Since the connecting site 66 is particularly at risk as a site for possible contamination, the device 49 provides a sterilant to the connecting site 66. The sterilant may be, for example, a flow of filtered air, a chemical sterilant, or a source of radiation. The device 49 may be of any biocompatible material and may be a molded article such as an injection molded piece of plastic or rubber. It may connect in an area adjacent the connecting site 66 either directly or by mating adaptors, known to one skilled in the art.

The device 49 has two compartments 102, 104. In the first compartment 102 the access means to the bulk container 14 are fitted to the device 49 at a connector site 112, closing the first compartment 102. The bulk container 14 may be engaged in the connector site 112 in a number of ways. As one example, there may be a snap-fit arrangement in which, during insertion, the bulk container 14 forces a wall of the connector site 112 to expand and, when the bulk container 14 is fully engaged, the wall snaps back into its static position. As another example, there may be external threads on the bulk container 14 and mating threads on the internal walls of the connector site 112. Still another example is a connector site 112 that is made of a deformable material such as rubber. The bulk container 14, during insertion, could expand the walls of the connector site 112 with the walls remaining in a deformed position while the bulk container 14 was engaged. Other attachment devices could also be used.

The second compartment 104 houses the connecting site 66 and also provides sterilant. The first 102 and second 104 compartments may be separated by a rigid membrane 116 which supports an engaging projection 118 and a receiving projection 120. The engaging projection 118 penetrates the bulk container 14 and provides a channel 106 for flow of fluid 23 from the bulk container 14 to the connecting site 66. In one embodiment, engaging projection 118 has a tip that is sufficiently sharp to pierce a septum 124 of the bulk container. Another method by which the engaging projection 118 could engage the bulk container 14 are threads on the projection 118 and corresponding threads on the container 14. Yet another means would be a snap fit between the container 14 and the projection 118. Within both the engaging 118 and receiving 120 projections there is the fluid channel 106. The fluid channel 106 provides the pathway for flow of fluid 23 from the bulk container 14 through the connecting site 66 and into the dose and/or delivery container 16. In one embodiment, the axis of the receiving projection 120 is aligned with the axis of the engaging projection 118 to provide a straight fluid flow pathway.

To evacuate fluid 23 from the bulk container 14, there is a second channel 126 in the first compartment 102. The channel 126 contains a filter 128 and provides access to normal atmospheric pressure, allowing fluid 23 to be drawn out of the bulk container 14. This access channel 126 transverses the interiors of the engaging projection 118 and the rigid membrane 116.

The second compartment 104 terminates in a door 130 or other means that provides controlled access to the septum 67 of the connecting site 66. The door 130 shields the receiving projection 120 from the environment when the dose and/or delivery container 16 is not operatively connected for filling. The door 130 opens inwardly to the second compartment 104 upon engagement of the dose and/or delivery container 16 or its connecting line 18, and retracts to a closed position when not so engaged. The door 130 does not create a total seal; however, it generally seals the second compartment 104 when not contacting the receiving projection 120.

The shielding device 49 allows the connecting site 66 access to a sterilant as previously described. In one embodiment of the invention, the second compartment 104 has a conduit 69 in its wall located to provide a sterilant to the connecting site 66, particularly the portion of the connecting site 66 that is engaged upon connection in the system 10. Through this conduit 69, the connecting site 66 may be operatively connected to a stream of filtered air 80 such as HEPA-filtered air forced into the second compartment 104 from a source (not shown). The flow of air 80 is oriented so that it provides a unidirectional non-recirculating flow from its source, across the septum 67 or other access means at the connecting site 66, and out of the second compartment 104 through the door 130. In this way, the connecting site 66 is exposed to a clean-room type of environment when fluid 23 from a bulk container 14 is operably accessible at the connecting site 66. When the connecting site 66 is not operably connected to a bulk container 14 of fluid 23, the flow of air 80 in the second compartment 104 may be halted to decrease or conserve the supply of filtered air 80. The second compartment 104 also prevents or minimizes an operator from making contact with the connecting site 66 when operating the system 10 or manually changing the bulk container 14. The positive outward flow of air 80 prevents egress of contamination any time that the bulk supply 14 is removed from the system 10.

The conduit 69 may alternatively provide the connecting site 66 access to a chemical sterilant. The chemical sterilant may be a peroxide such as hydrogen peroxide or other chemical sterilant known in the art. The source of sterilant may be located outside of the compartment 104 and directed into the compartment 104 by, for example, an aerosol or stream. Alternatively, the source of sterilant may be located within the compartment 104.

Still another method to maintain a sterile connecting site 66 is by directing radiation from a source into the second compartment 104 and directed to irradiate the connecting site 66. A radiation source such as a source of ultraviolet radiation at a wavelength of less than 400 nm is positioned to direct radiation to the connecting site 66. The radiation source may be positioned within the compartment 104 or may be positioned outside of the compartment 104 if the radiation can penetrate the compartment 104 to irradiate the connecting site 66.

In one embodiment, the system 10 contains a sensor 71 that will either alert the operator that the bulk container 14 has a predetermined volume of fluid 23 remaining, and/or disengage access to the connecting site 66 of a first bulk container 14 and engage the connecting site 66a of the second bulk container 14a. The sensor 71 may be activated using, for example, optical, electronic or other means. Upon detection of the signal emitted by the sensor 71, the system 10 may automatically engage a fresh bulk container 14a without disruption of the transfer sequence of fluid 23 into the dose and/or delivery container 16. In this way, the entire volume of fluid 23 from each bulk container 14, 14a may be utilized, which minimizes waste of fluid 23.

In another embodiment, the system 10 contains one or more air detection sensors 73 to facilitate bubble detection and/or removal along a fluid path, as described in U.S. Pat. No. 5,868,710 entitled Medical Fluid Injector which is expressly incorporated by reference herein in its entirety. The air detection sensors 73 may be positioned anywhere along the fluid path, but are most helpful if located at least at points of fluid transfer, such as at a connecting site 66, at entry and exit ports into and out of a dose and/or delivery container 16, etc. Briefly, the sensors 73 detect the diffraction of light at an air/fluid or air/solid boundary, the air causing light rays to deviate substantially from their normal path. The sensor 73 is thus light-sensitive and produces a signal indicating failure to receive light due to the presence of air. The system 10 may contain a prime or flush mechanism to remove the air bubbles and/or may not engage until an operator has taken steps to remove the air bubbles. The fluid 23 infused into a patient at the desired time is thus free of air bubbles.

Figure 3:
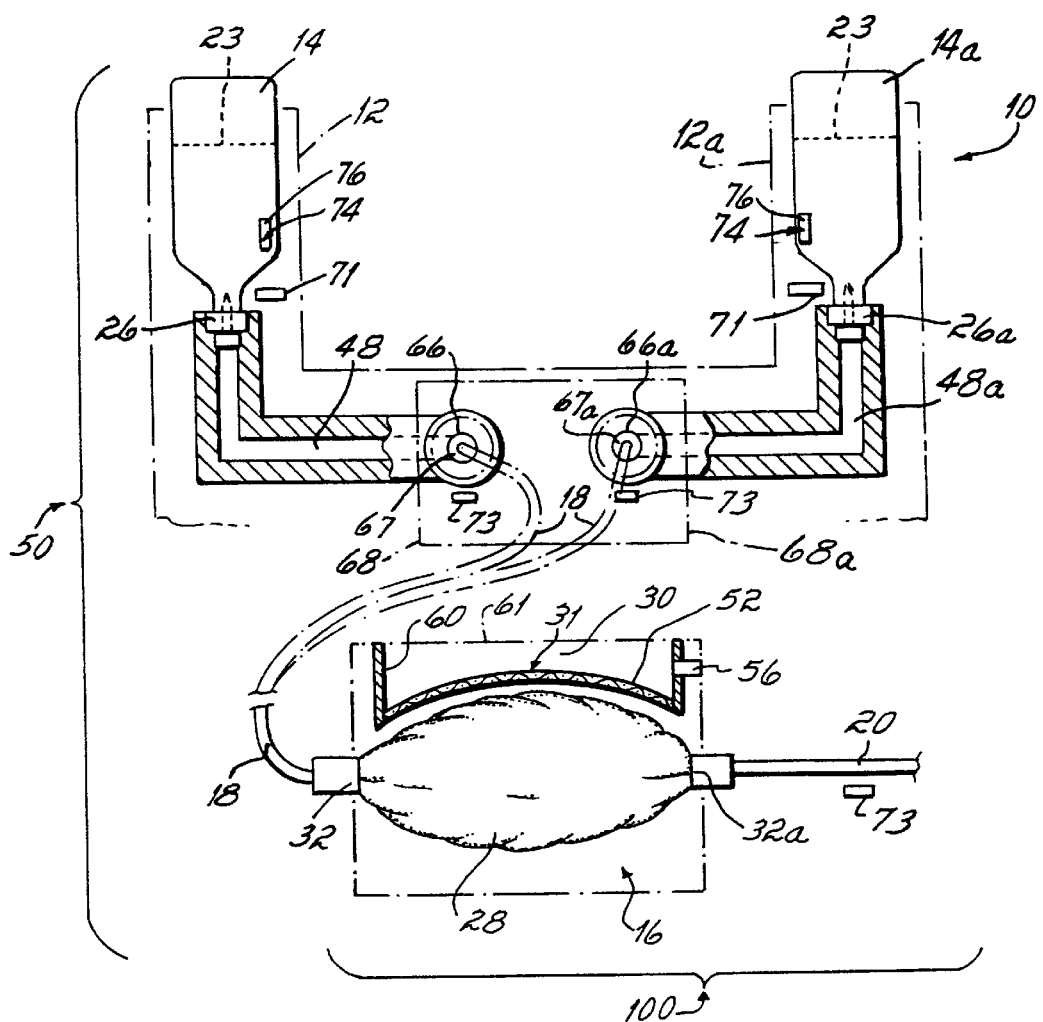
FIG. 3 shows the system of FIG. 1 with a flexible wall dose and/or delivery container.

With reference to FIG. 3 showing one embodiment of the invention, the delivery container 16 has at least one flexible or semi-flexible wall 29 and is hereinafter referred to as a flexible wall container 27. An example of this type of delivery container 16 is a bag 28, such as a typical intravenous fluid bag 28. It will be appreciated that other deformable delivery containers 16 may also be used, including compartmentalized strips or blister packages. Multiple compartments, such as those made by heat sealing, layering sheets, molding separate reservoirs, etc. may contain multiple medical fluids. The multiple compartments may be joined to a patient line 20 by valving, Y-connectors, piercing, unclamping, crushing or snapping.

The delivery container 16 in this embodiment may have an external rigid sleeve and port with a flexible inner bag similar to some types of baby bottles. The flexible wall container 27 such as a bag 28 may be made of any type of material capable of withstanding sterilization and containing sterile fluid 23, for example, resilient plastic that retains a specific form, plastic that completely collapses, etc. In the system 10, a flexible wall container 27 that is prefilled with fluid 23 may be used. Alternatively, an empty flexible wall container 27 may be filled with fluid 23 from a bulk container 14 as previously described.

In use, fluid 23 is delivered from the flexible wall container 27 to the patient line 20 by providing pressure to at least one flexible wall 29. Pressure may be applied directly to the at least one flexible wall 29 of the container 27, or alternatively as shown, pressure may be applied indirectly to the at least one flexible wall 29 by applying pressure to a pressurizeable chamber 30 adjacent the at least one flexible wall 29 of the container 27. Pressure may be provided by, for example, hydraulic means, mechanical means, pneumatic means, etc. from a source 56. The chamber 30 may have a clamshell-type opening to house the container 27, with at least one side 31 of the chamber 30 capable of applying a pressure. The position of the container 27 within the chamber 30 maybe located by a number of indices such as pins, nubs, ribs, holes, etc. One surface of the chamber 30 may be transparent to allow the operator to view the container 27 housed therein. The container 27 may be completely contacted by the pressurizeable chamber 30 or have only the flexible wall 29 adjacent the side 31 of the chamber 30 capable of applying a pressure. The flexible wall container 27 may be fitted into the pressurizeable chamber 30, covering the entrance by a molded-in fitting that interlocks with the walls of the chamber 30. The container 27 may be locked in place by turning a hard fitting on the chamber 30. The fitting and opening may be on the sides or the back of the container 27. Alternatively, the container 27 may have a patient connector 20 which may protrude through an opening in the chamber 30.

The pressurizeable chamber 30 contains a membrane 52 on at least one surface that is capable of exerting a desired pressure on the flexible wall 29 of the container 27. The membrane 52 is made of a material that is capable of withstanding the desired pressure with which to deliver the fluid 23. For example, if the fluid 23 is a contrast agent to be administered to a patient in preparation for an imaging procedure, the required pressure depends upon the particular imaging procedure to be performed. Pressures may range from as low as about 100 pounds per square inch (psi) to a pressure of about 1200 psi that is used in angiography. To achieve different pressures, different types of membranes 52 may be used, or alternatively a membrane 52 capable of withstanding the maximum pressure for any procedure may be used.

The pressurizeable chamber 30 may include at least a partial frame or holder 60 to provide a rigid outer shape. The holder 60 may provide a handle (not shown) for holding and manipulating the container 27. The holder 60 may provide locating features (not shown) for locating or translating the container 27 into a pressurizeable chamber 30 and/or for positioning the container 27 into or out of a position for injecting the contained fluid 23. The holder 60 may be made of any rigid material such as metal, plastic, plexiglass, or the like. The holder 60 may be adapted to operably connect the membrane 52 with an external pressure source (not shown). In an alternative embodiment, pressure may be applied by manual or automated pressing, squeezing, rolling, and so on. In this embodiment, only the pressurized membrane 52, rather than the flexible wall container 27, receives pressure. Therefore, the container 27 need not meet exacting pressure tolerances in its manufacture. Such a dose and/or delivery container 16 is less costly to manufacture than one which would have to withstand direct application of pressure. This also minimizes any chance of breaking the integrity of the container 27, which would possibly compromise the sterility of the fluid 23 and/or cause leakage of fluid 23 from the container 27.

When both component paths 50, 100 of the system 10 are used, a bulk container 14 of fluid 23 is operably connected to the system 10. This may be accomplished by seating the bulk container 14 in a holder 12 so as to initiate a flow of fluid 23 from the bulk container 14 to a connecting site 66, which may either be integral with the bulk container 14 or attached to the bulk container 14 with a connector 48. A dose and/or delivery container 16 having a connector line 18 is operable attached at connecting site 66. The connector line 18 may be fitted with luer-type connectors (not shown) for a secure but resealable seal, and is made of any standard hospital grade sterile tubing such as Tygon® tubing. The flow of fluid 23 into the delivery container 16 from the bulk container 14 is initiated by any number of mechanisms, including gravity, vacuum, pressurization, pumping, squeezing, rolling, or other fluid displacement techniques. After the desired volume of fluid 23 has entered or filled the container 27, either directly or through a connector line 18, the container 27 is irreversibly disconnected, either directly or through connector line 18 from connecting site 66. Any subsequent attempt to operatively reconnect connector line 18 at connecting site 66 is prevented by, for example, configuring connector line 18 with a breakaway or removable cannula (not shown) that must be removed before the connector line 18 can be applied. Access to connecting site 66 would require removing this cannula. Other methods to prevent reconnection are also possible.

Flow of fluid 23 from the flexible wall container 27 may then be initiated into a patient through patient connector line 20. This may be performed immediately after filling and disconnecting the flexible wall container 27 from the bulk source 14, or may be performed at a later time. As previously described, a flexible wall container 27 that has been prefilled, either at the site of manufacture or manually by a technologist, may be used. The system 10 in use delivers a medical fluid 23 to a patient in a conventional manner, as known to one skilled in the art. The delivery container 16 contains at least one port 32 for connecting either directly or indirectly to a patient connector line 20 for administration of fluid 23 into a patient at an infusion site. In one embodiment, the system contains a device to detect extravasation of the fluid 23 at the patient infusion site, which either prompts the operator for action and/or terminates the process. Such a device is disclosed in WO 99/15074 based on U.S. Patent Application No. 60/059,749 entitled Optical Extravasation Detection Method and Apparatus, which is expressly incorporated by reference herein in its entirety.

A flexible wall container 27 such as a bag 28 may be of any shape, for example, round, oval, elliptical, rectangular, etc. The bag 28 may assume many configurations, such as a bag 28 having channels or directed fluid paths as disclosed in U.S. Pat. No. 5,779,693 entitled Flexible Plastic Container for the Containment and Delivery of Diagnostic Contrast Media and Parenteral Drug Formulations, which is hereby incorporated by reference herein in its entirety. With fluid 23 contained in a bag 28, an equal pressure may be applied to all surfaces of the fluid 23, unlike a syringe in which only unidirectional pressure is typically applied to the fluid 23 contained therein. The bag 28 may have integral graphics or textural features whose visual appearance changes upon contact of the wall 29 with fluid 23, thereby visually indicating that fluid 23 is present in the bag 28. While a bag 28 may be sterilized and reused, it is preferred to dispose of the bag 28 after each use. A bag 28 also requires less area for disposal, both because of its flexibility to be rolled or folded to further decrease its area, and also because it is collapsible upon removal of fluid 23 from its interior. The bag 28 may be collapsible by folding in on itself. The material, geometry and form of the bag 28 may have features such as pleated sides to minimize entrapment of fluid 23 as the bag 28 collapses.

The bag 28 has at least one port 32 for at least one connector line 18, 20. The port 32 is used to attach the bag 28 by a connector line 18 to the connecting site 66 to transfer fluid 23 from a bulk source 14. After transfer of the desired volume of fluid 23 into the bag 28 and disconnection of either the bag itself 28 or the connector 18 from connecting site 66, the port 32 may be sealed. Alternatively, a patient connector line 20 may be attached at either the same port 32 or at a different port 32a for allowing fluid transfer to an infusion site in a patient. The connector lines 18, 20 may already be pre-attached to the bag 28 or other delivery container 16. In an embodiment in which both connector lines 18, 20 are pre-attached, the bag 28 must necessarily have at least two ports 32, 32a. The lines 18, 20 may connect to the port 32, 32a in any standard manner known to one skilled in the art, for example with luer-type connectors (not shown). The desired volume of fluid 23 may be administered to a patient either immediately upon filling of a delivery container 16 and disconnection of connector line 18 from the connecting site 66, or at any time thereafter. The flexible wall delivery container 27 may also be pre-filled with the desired fluid 23 and inserted into the system 10 without being filled from a bulk source 14. The pre-filled delivery container 27 may be purchased already containing fluid 23, or may have been previously filled from a bulk source 14 utilizing the system 10 or by other means, or may have been previously filled from a dose container 16.

Figure 4:
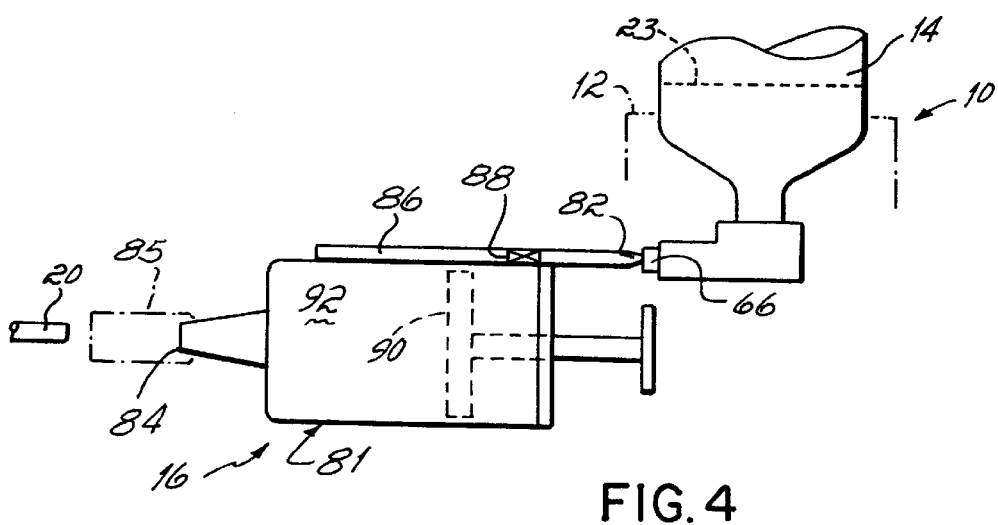
FIG. 4 shows a side view of the system of the invention with an inflexible wall dose and/or delivery container.

With reference to FIG. 4, a delivery container 16 having inflexible walls such as a syringe 81 may be used. In one embodiment, the syringe 81 has an independent filling port 82 and a separate discharge port 84. The filling port 82 is a tube or cannula 86 that is integral with and is located at the proximal end of the syringe 81. It contains a check valve 88 to permit only unidirectional flow of fluid 23 from the bulk source 14 into the syringe 81. When the filling port 82 is coupled at the connection site 66, either directly to bulk container 14 or through connector line 18 or through connector 48, and the discharge port 84 is sealed, for example, by a removable cap or frangible tip member 85, fluid 23 enters the tube or cannula 86. Refraction of the piston 90 forces fluid 23 to flow from the bulk supply 14 from the cannula 86 into the syringe barrel 92. After the desired volume of fluid 23 has been withdrawn from the bulk source 14, the filling port 82 is disconnected or decoupled from the connection site 66, thus preventing fluid 23 access from the bulk supply 14 to the syringe 81. The cap or tip member 85 is removed before connecting by either manual or automated means, the discharge port 84 of the syringe 81 to the patient connector line 20. The syringe 81 may be operated either manually or in a power injection system. Essentially all of the fluid 23 contained within the syringe 81 may be expelled.

A delivery container 16 having inflexible walls such as syringe 81 has several limitations that are not encountered when using a flexible wall container 27. One drawback with a syringe 81 is the need for lubricant chemicals such as silicone to lubricate the moveable piston 90. Another drawback is the increased cost of a syringe 81 due at least in part to the stringent manufacturing tolerances and the lubricants required for a secure fit of component parts. Still other drawbacks are the lower shipping units per container due to the rigid structure as compared to a flexible wall container 27, lower disposal volume per unit area, and the need for protective packaging to minimize potential damage to the rigid walls during transport.

The volume of fluid 23 that is transferred from the bulk source 14 to a dose and/or delivery container 16 is substantially the volume that is to be administered to a patient. The dose and/or delivery container 16 is referred to herein as being filled with fluid 23 although the entire volume of the container 16 may not be occupied with the fluid 23.

The system 10 may be configured either as a single unit or in modules. For example, a modular system may encompass unit 50 of a fluid path between the bulk source 14 and a dose and/or delivery container 16, or unit 100 of a fluid path between the dose and/or delivery container 16 and the patient line 20. A modular system may be used, for example, if size and/or weight of a single unit is prohibitive.

In one embodiment, an operator is prompted at the conclusion of a procedure on one patient by an operator interface system to enter patient- and procedure-specific parameters for a subsequent patient to be imaged. Determination of these parameters may be by various manual methods and/or computer implemented algorithms, as disclosed in U.S. Pat. No. 5,583,902 entitled Method of and Apparatus for Predicting Computed Tomography Contrast Enhancement, which is expressly incorporated by reference herein in its entirety. A variable number of patient specific parameters may be used in calculating the optimal volume of fluid 23. Examples include body mass, weight, volume of distribution, total plasma clearance, parameters of renal excretion such as glomerular filtration, tubular secretion, and tubular reabsorption, parameters of liver function such as enzyme and protein levels, and parameters of cardiac function such as blood flow and blood pressure, just to name a few. The system 10 then automatically initiates transfer of the required volume of fluid 23 into the dose and/or delivery container 16. If the bulk source 14 becomes depleted during the transfer, the system 10 automatically switches to a second bulk source 14a by mechanically withdrawing connector line 18 from connecting site 66 and reconnecting to the connecting site 66a for bulk supply 14a. The connecting and reconnecting may be accomplished using an automated or manual method. Transfer of fluid 23 resumes until the desired volume entered the dose and/or delivery container 16. The system 10 continuously monitors the path of fluid 23 for the presence of air using sensors 73 and automatically purges the system 10 and/or prompts the operator. Upon completion of transfer of fluid 23 to a dose and/or delivery container, an interface system may alert the operator that the fluid 23 is ready for administration. During administration, the sensors 73 actively monitor the path of fluid 23 for air bubbles and automatically shuts down the injection and/or alerts the operator if bubbles are detected.

The system 10 may be configured so that system, procedure and/or patient information may be communicated to a network. For example, the bulk container 14 may have an integral magnetic strip 74 containing information about the bulk container 14 and its contents such as identity, lot number, expiration date, brand, manufacturer, clinical indications, time of use and number of uses. The magnetic strip may be written to by the delivery container 16. The magnetic strip may also contain information intended to be communicated from the manufacturer to the clinicians or technologists using the product. The encoded information may be written to or read by a variety of means such as optical etching or radiofrequency. As another example, the dose and/or delivery container 16 may also contain a similar magnetic strip containing the above-described written or read information.

The system 10 may be linked to a purchasing network. In this embodiment, the bulk container 14 and/or dose and/or delivery container 16 may contain an identifier 76 such as a magnetic strip 74 that is readable by a computerized information system, such as an inventory tracking system used by a purchasing department. The identifier 76 may be a sticker containing, for example, a bar code, a radiofrequency source, or a microchip, and may contain a variety of information such as product name, source, concentration, lot number, expiration date, whether the package had been previously used, etc. The computerized information system may track the volume of fluid 23 either removed and/or remaining in the bulk source 14, 14a, and/or the number of bulk source packages 14, 14a placed in or removed from holders 12, 12a. Using this information, a purchasing system may quickly update its orders for a new supply of bulk source packages 14, 14a to maintain a desired level of inventory.

The invention has numerous advantages, the following being illustrative and not limiting examples. One advantage of the invention is that there is a substantially reduced risk of patient and fluid 23 contamination, yielding greater safety in administering medical fluids to patients. Another advantage is that standard size bulk contrast supply packages 14, 14a may be used, thereby eliminating numerous package sizes and separate dose and/or delivery container 16 filling steps. Still another advantage is that the invention allows optimization of the volume of fluid 23 such as contrast agent injected into each patient for desired image quality and patient safety. Yet another advantage is the cost and time efficiency from the system 10 as compared to individual components.

It should be understood that the embodiments of the present invention shown and described in the specification are only specific embodiments of the inventors who are skilled in the art and are not limiting in any way. For example, an intelligent interface with the imaging equipment may be provided. This would facilitate automatic start/stop of the injecting and/or imaging apparatus, and allow data transfer between these systems. Therefore, various changes, modifications or alterations to these embodiments may be made or resorted to without departing from the spirit of the invention and the scope of the following claims.

What is claimed is:

1. A method of delivering a medical fluid to a patient comprising:
   providing a plurality of unit doses of the medical fluid in a bulk container,
   coupling a fill line of a delivery container selected from a plurality of delivery containers to a single connecting site of the bulk container,
   transferring one of the unit doses of medical fluid through the fill line to a reservoir of the delivery container,
   disconnecting the fill line of the delivery container irreversibly from the connecting site,
   administering the unit dose of medical fluid from the delivery container through a patient connector line to an infusion site in the patient after disconnecting the fill line from the connecting site, and
   discarding the fill line, the patient connector line and the delivery container after administering the unit dose of medical fluid to the infusion site.

2. The method of claim 1 wherein fluid flow is initiated by a method selected from the group consisting of gravity, pumping, mechanical pressure, hydraulic pressure, vacuum and combinations thereof.

3. The method of claim 1 wherein the delivery container has at least one flexible wall that contacts a pressurizeable chamber, and administering the unit dose of medical fluid further comprises:

delivering the unit dose of medical fluid to the infusion site by pressurizing the pressurizeable chamber.

4. The method of claim 3 wherein the chamber is pressurized through action of a pressure selected from the group consisting of hydraulic, mechanical, pneumatic and combinations thereof.

5. The method of claim 1 further comprising:

determining a customized volume for the unit dose of medical fluid transferred through the fill line to the reservoir of the delivery container.

6. The method of claim 5 wherein the customized volume is determined using at least one of patient specific data and procedure specific data.

7. The method of claim 1 wherein the steps of providing, transferring, disconnecting, and administering are performed substantially by automation.

8. The method of claim 1 further comprising:

determining a customized volume for the unit dose of medical fluid by an algorithm using at least one of patient specific data and procedure specific data.

9. The method of claim 1 further comprising:

providing a device to detect extravasation of medical fluid at the infusion site.

10. The method of claim 1 further comprising:

tracking a cumulative volume of medical fluid removed from the bulk container.

11. The method of claim 1 further comprising:

providing a plurality of delivery containers, each serially receiving a corresponding one of the unit doses of medical fluid from the bulk container at the connecting site, and tracking a number of the plurality of delivery containers receiving medical fluid.

12. A method of delivering medical fluid to a patient comprising:

providing a system including
  a bulk container holding a plurality of unit doses of medical fluid and a single connecting site,
  a delivery container operatively connectable to the connecting site to receive one of the plurality of unit doses of medical fluid from the bulk container,
  a patient connector line for administering the unit dose of medical fluid from the delivery container to an infusion site in the patient, and
  a fill line capable of being connected in fluid communication with the single connecting site for transferring medical fluid from the bulk container to the delivery container and of being irreversibly disconnected from the connecting site, transferring the unit dose of medical fluid through the fill line to a reservoir of the delivery container, disconnecting the fill line of the delivery container irreversibly from the connecting site, administering the unit dose of medical fluid from the delivery container through a patient connector line to an infusion site in the patient after disconnecting the fill line from the connecting site, and discarding the fill line, the patient connector line and the delivery container after administering the unit dose of medical fluid to the infusion site.

13. The method of claim 12 wherein the delivery container is a syringe comprising a barrel for containing the unit dose of medical fluid, a filling port comprising a tube and a check valve, a discharge port, and a piston for discharging the unit dose of medical fluid through the discharge port, wherein the syringe is filled by sealing the discharge port to prevent fluid release, retracting the piston to allow fluid into the barrel and then sealing the filling port with the check valve to prevent further fluid in the barrel.

14. A method for providing medical fluid to a patient, comprising:

providing a bulk container containing a volume of medical fluid, determining a customized supply of medical fluid for administration to the patient that is less than the volume of medical fluid in the bulk container, coupling a fill line of a delivery container selected from a plurality of delivery containers to a single connecting site of the bulk container, transferring the customized supply of medical fluid through the fill line to a reservoir of the delivery container, disconnecting the fill line of the delivery container irreversibly from the connecting site, administering the customized supply of medical fluid from the delivery container through a patient connector line to an infusion site in the patient after disconnecting the fill line from the connecting site, and discarding the fill line, the patient connector line and the delivery container after administering the customized supply of medical fluid to the infusion site.

15. The method of claim 14 wherein the delivery container is selected from the group consisting of a bag and a syringe.

16. The method of claim 14 wherein the delivery container is a bag contacting a pressurizeable chamber and administering the customized supply further comprises:

providing a pressure to the pressurizeable chamber.

17. The method of claim 14 wherein the steps of providing, transferring, disconnecting, and administering are performed substantially by automation.

18. The method of claim 14 wherein the step of determining the customized supply forther comprises:

calculating a volume for the customized supply with an algorithm using at least one of patient specific data and procedure specific data.

19. The method of claim 14 further comprising:

flowing filtered air over the connecting site to maintain the sterility of the connecting site.

* * * * *

UNITED STATES PATENT AND TRADEMARK OFFICE
CERTIFICATE OF CORRECTION

PATENT NO.    : 6,623,455 B2
DATED         : September 23, 2003
INVENTOR(S)   : Small et al.

It is certified that error appears in the above-identified patent and that said Letters Patent is hereby corrected as shown below:

Column 10,
Line 18, reads "maybe located" and should read -- may be located --.

Column 15,
Line 58, subparagraph beginning with "transferring the unit" should not be double indented, "transferring" on line 58 should line up with "disconnecting" on line 60.

Column 16,
Line 55, reads "forther" and should read "farther".

Signed and Sealed this

Sixth Day of July, 2004

JON W. DUDAS
*Acting Director of the United States Patent and Trademark Office*